United States Patent
Yasukawa et al.

(10) Patent No.: US 6,897,312 B2
(45) Date of Patent: *May 24, 2005

(54) METHOD FOR PRODUCING HIGH MELTING POINT CRYSTALS OF PHENOXYPROPIONIC ACID DERIVATIVE

(75) Inventors: Masami Yasukawa, Yamaguchi (JP); Shinji Kuwahara, Yamaguchi (JP)

(73) Assignee: Nissan Chemical Industries, Ltd., Tokyo (JP)

(*) Notice: Subject to any disclaimer, the term of this patent is extended or adjusted under 35 U.S.C. 154(b) by 494 days.

This patent is subject to a terminal disclaimer.

(21) Appl. No.: 10/000,011

(22) Filed: Dec. 4, 2001

(65) Prior Publication Data

US 2002/0055634 A1 May 9, 2002

Related U.S. Application Data

(63) Continuation of application No. 09/674,282, filed as application No. PCT/JP99/01979 on Apr. 14, 1999, now Pat. No. 6,353,104.

(30) Foreign Application Priority Data

Apr. 28, 1998 (JP) ............................................ 10-118456

(51) Int. Cl.⁷ ....................... C07D 241/36; A01N 43/60
(52) U.S. Cl. ...................................... 544/354; 504/235
(58) Field of Search ........................... 544/354; 504/235

(56) References Cited

FOREIGN PATENT DOCUMENTS

JP  2-2145050  8/1990

OTHER PUBLICATIONS

Chemical Abstracts, vol. 127, No. 8, Aug. 18, 1997, Miyake, et al., "Crystallization Behaviors of Alpha– and Beta–Quizalofop–ethyl Polymorphs in Homogeneous Nucleation," XP002133704, Abstract No. 91664z, pp. 101–110.
Chemical Abstracts, vol. 105, No. 15, Oct. 20, 1986, Makino et al., "Crystal Structure of a New Herbicide, Ethyl 2-(4-(6-chloro-2-quinoxalinyloxy)phenox)propanate," XP002133705, Abstract No. 143938j, pp. 237–243.
McGraw–Hill Encyclopedia of Science and Technology, vol. 14, p. 149, 1987.
Van Nostrands's Scientific Encyclopedia, Van Nostrand Reinhold, 8th Edition, p. 2057, 1995.
U. Mueller, Inorganic Structural Chemistry, John Wiley & Sons, pp. 14, 15 and 21, 1993.

*Primary Examiner*—Alan L. Rotman
*Assistant Examiner*—Tamthom N. Truong
(74) *Attorney, Agent, or Firm*—Oblon, Spivak, McClelland, Maier & Neustadt, P.C.

(57) ABSTRACT

A method for producing β crystals of ethyl (R)-2-[4-(6-chloro-2-quinoxalin-2-yloxy)phenoxy]propionate, which is characterized by heating α crystals, or α crystals and β crystals, within a range of from 50° C. to lower than the melting point of the α crystals.

7 Claims, No Drawings

METHOD FOR PRODUCING HIGH MELTING POINT CRYSTALS OF PHENOXYPROPIONIC ACID DERIVATIVE

This application is a continuation of application Ser. No. 09/674,282, filed Oct. 30, 2000, now U.S. Pat. No. 6,353,104, which is a 371 of PCT/JP99/01979, filed Apr. 14, 1999.

TECHNICAL FIELD

The present invention relates to a method for producing high melting point crystals (hereinafter referred to as β-crystals) of ethyl(R)-2-[4-(6-chloroquinoxalin-2-yloxy) phenoxy]propionate (hereinafter referred to as quizalofop-p-ethyl) and β-crystals thereby produced.

BACKGROUND ART

Quizalofop-p-ethyl which is useful as an active ingredient for a herbicide, is known to have two types of crystal forms, i.e. low melting point crystals (hereinafter referred to as α-crystals) and β-crystals. JP-B-4-76721 discloses that β-crystals can be produced by gradually cooling a solution having quizalofop-p-ethyl dissolved in a solvent, with stirring and maintaining it at a crystallizing temperature, and the produced β-crystals are ones having crystallites of at most 1 μm agglomerated, whereby in some cases, transfer of the solvent slurry, or filtration and drying of the precipitated crystals, are difficult.

DISCLOSURE OF INVENTION

It is an object of the present invention to provide β-crystals which are easy to handle in an industrial scale and a method for their production.

The present invention provides a method for producing β-crystals, which is characterized by heating quizalofop-p-ethyl in the form of α-crystals, or α-crystals and β-crystals, within a range of from 50° C. to lower than the melting point of α-crystals, and β-crystals produced by such a method.

The heating can be carried out by heating in contact with a high temperature innert gas (hereinafter referred to as a gas-solid heating method), heating with mixing in a solid state (hereinafter referred to as a solid heating method) or heating in suspension with a hardly soluble solvent (hereinafter referred to as a suspension heating method).

The gas-solid heating method may, for example, be a method wherein quizalofop-p-ethyl is charged into an apparatus equipped with a gas-solid contact function such as a pneumatic conveying dryer, a fluidized bed dryer, a circulation dryer or a hot air dryer, and a high temperature gas such as heated air or heated nitrogen is blown thereinto for heat treatment.

The solid heating method may, for example, be a method wherein quizalofop-p-ethyl is charged into an apparatus equipped with a heating means such as a jacketed kneader, an agitation drier, a jacketed screw conveyer or a conical drier and provided with a mixing function, and heated and mixed for a predetermined period of time.

The suspension heating method may, for example, be a method wherein quizalofop-p-ethyl is charged to a hardly soluble solvent such as water or ethylene glycol, and heated in suspension.

The heating can be carried out usually at a temperature of from 50° C. to lower than the melting point of α-crystals, preferably from 65° C. to lower than the melting point of α-crystals.

The heating time usually depends on the heating temperature and is required to be a time until α-crystals have substantially disappeared. For example, it takes at least 100 hours when heating is carried out at 60° C. and a few hours when heating is carried out at 70° C., to obtain β-crystals.

After α-crystals have been converted to β-crystals by heating, cooling, or cooling followed by filtration in the suspension heating method, is carried out to obtain β-crystals.

In the gas-solid heating method and the solid heating method, β-crystals can be obtained in a solid state, and can be used as it is, or after pulverization, for example, for the production of an aqueous suspension concentrate.

Further, in the gas-solid heating method or the solid heating method, if quizalofop-p-ethyl mainly in the form of α-crystals produced by crystallization method, is employed, the resulting β-crystals will be obtained in a powder form without forming a block solid in the above apparatus, whereby high productivity can be maintained. In such a case, it is preferred to employ quizalofop-p-ethyl mainly in the form of α-crystals containing substantially no solvent for crystallization. JP-B-2-214504 discloses that α-crystals obtained as a wet product by a crystallization method may sometimes change into β-crystals when dried at a temperature exceeding 70° C. for at least 5 hours. However, if such a wet product containing a solvent for crystallization is used, dissolution by the solvent takes place during the heating, and the product is likely to be an aggregated solid in the apparatus, whereby industrial operation is practically difficult.

In the suspension heating method, removal of the hardly soluble solvent may sometimes be required. For example, when the hardly soluble solvent is water, a drying step may sometimes be required. However, in a case where an aqueous suspension agricultural chemical composition is to be obtained, drying will not be required depending upon the weight concentration of the suspension. Further, by the suspension heating method, the dispersed state in the apparatus can be excellently maintained during the heating operation, whereby the temperature control of quizalofop-p-ethyl is easy, and uniform β-crystals can be produced efficiently. Further, β-crystals formed by the suspension heating method are excellent in the filtration property and easy for drying.

Now, a method for obtaining desired β-crystals by suspending the starting material in water which is the hardly soluble solvent and which is industrially inexpensive, will be described.

Namely, quizalofop-p-ethyl in the form of α-crystals, or α-crystals and β-crystals, is suspended in water usually in an amount of from 0.1 to 60 wt %, preferably from 1 to 60 wt %, and the suspension is maintained at a temperature of from 50° C. to lower than the melting point of α-crystals until α-crystals substantially disappears, preferably at a temperature of from 65° C. to lower than the melting point of α-crystals for from 10 minutes to 48 hours. Thereafter, it is cooled to a temperature where usually filtration can be carried out, usually at most 50° C., preferably at most 40° C., followed by filtration to collect crystals. When the crystals have been completely converted to β-crystals, drying of the crystals can be carried out at a temperature lower than the melting point of β-crystals, usually lower than the melting point of α-crystals, preferably at most 65° C.

BEST MODE FOR CARRYING OUT THE INVENTION

Now, the present invention will be described in further detail with reference to Examples. However, it should be understood that the present invention is by no means restricted to such specific Examples. The weight ratio of α-crystals and β-crystals approximates the area ratio of the respective endothermic peaks obtained by the differential scanning calorimetry and thus was obtained from the area ratio of the respective endothermic peaks.

EXAMPLE 1

Into a 20 l double-screw U-trough type jacketed kneader, 20 kg of α-crystals of quizalofop-p-ethyl containing 0.2 wt % of β-crystals, were charged and mixed. Warm water was circulated to the jacket to raise the temperature to 70° C. Four hours later, the differential scanning calorimetry of quizalofop-p-ethyl was carried out, whereby it was confirmed that the entire amount had been converted to β-crystals.

EXAMPLE 2

In the same manner as in Example 1, heating was carried out at 65° C. for 16 hours, and then the differential scanning calorimetry of quizalofop-p-ethyl was carried out, whereby it was confirmed that the entire amount had been converted to β-crystals.

EXAMPLE 3

Into a 10 l agitation drier, 5 kg of α-crystals of quizalofop-p-ethyl containing 0.2 wt % of β-crystals, were charged and mixed. Warm water was circulated to the jacket to raise the temperature to 72.5° C. Two hours later, the differential scanning calorimetry of quizalofop-p-ethyl was carried out, whereby it was confirmed that the entire amount had been converted to β-crystals.

EXAMPLE 4

Into a 5 l conical drier, 1 kg of α-crystals of quizalofop-p-ethyl containing 0.2 wt % of β-crystals, were charged and mixed. Warm water was circulated to the jacket to raise the temperature to 55° C. Two months later, the differential scanning calorimetry of quizalofop-p-ethyl was carried out, whereby it was confirmed that the entire amount had been converted to β-crystals.

EXAMPLE 5

Into a 10 l conical flash drier, 3 kg of α-crystals of quizalofop-p-ethyl containing 0.2 wt % of β-crystals, were charged, and hot air was blown into it to raise the temperature to 70° C. Four hours later, the differential scanning calorimetry of quizalofop-p-ethyl was carried out, whereby it was confirmed that the entire amount had been converted to β-crystals.

EXAMPLE 6

In the same manner as in Example 5, heating was carried out at 65° C. for 16 hours. Then, the differential scanning calorimetry of quizalofop-p-ethyl was carried out, whereby it was confirmed that the entire amount had been converted to β-crystals.

EXAMPLE 7

Into a 5 l fluidized drier, 1 kg of α-crystals of quizalofop-p-ethyl containing 0.2 wt % of β-crystals, was charged and hot air was blown into it to raise the temperature to 70° C. Four hours later, the differential scanning calorimetry of quizalofop-p-ethyl was carried out, whereby it was confirmed that the entire amount had been converted to β-crystals.

EXAMPLE 8

Into a 2 l jacketed reaction flask, 60 g of α-crystals of quizalofop-p-ethyl containing 0.2 wt % of crystals, and 240 g of water, were charged to prepare a 20 wt % suspension solution. Warm water was circulated to the jacket, and the suspension solution was heated to 72.5° C. with stirring. Two hours later, a part of quizalofop-p-ethyl suspended in the solution, was collected by filtration and dried, whereupon the differential scanning calorimetry was carried out, whereby it was confirmed that the entire amount had been converted to β-crystals.

Then, the warm water in the jacket was withdrawn, and the above suspension solution was cooled. After cooling, quizalofop-p-ethyl suspended in the solution was collected by filtration at room temperature and dried at about 55° C. Then, the differential scanning calorimetry was carried out, whereby it was confirmed that the entire amount was maintained to be β-crystals.

EXAMPLE 9

Into a 2 l jacketed reaction flask, 120 g of α-crystals of quizalofop-p-ethyl containing 0.2 wt % of β-crystals, and 180 g of water, were charged to prepare a 40 wt % suspension solution. Warm water was circulated to the jacket, and the suspension solution was heated to 70° C. with stirring. Twenty hours later, a part of quizalofop-p-ethyl suspended in the solution was collected by filtration and dried at 45° C. Then, the differential scanning calorimetry was carried out, whereby it was confirmed that the entire amount had been converted to β-crystals.

EXAMPLE 10

Into a 2 l jacketed reaction flask, 40 g of α-crystals of quizalofop-p-ethyl containing 10 wt % of β-crystals, and 240 g of water, were charged to prepare an about 14 wt % suspension solution. Warm water was circulated to the jacket, and the suspension solution was heated to 70° C. with stirring. Four hours later, a part of quizalofop-p-ethyl suspended in the solution was collected by filtration and dried. Then, the differential scanning calorimetry was carried out, whereby it was confirmed that the entire amount had been converted to β-crystals.

Then, the warm water in the jacket was withdrawn, and the above suspension solution was cooled. After cooling, quizalofop-p-ethyl suspended in the solution was collected by filtration and dried at about 50° C. Then, the differential scanning calorimetry was carried out, whereby it was confirmed that the entire amount was maintained to be β-crystals.

EXAMPLE 11

Into a 2 l jacketed reaction flask, 15 g of α-crystals of quizalofop-p-ethyl containing 10 wt % of β-crystals, and 240 g of water, were charged to obtain an about 6 wt % suspension solution. Warm water was circulated to the jacket, and the suspension solution was heated to 70° C. with stirring. Six hours later, a part of quizalofop-p-ethyl suspended in the solution was collected by filtration and dried. Then, the differential scanning calorimetry was carried out, whereby it was confirmed that the entire amount had been converted to β-crystals.

Then, the warm water in the jacket was withdrawn, and the above suspension solution was cooled. After cooling, quizalofop-p-ethyl suspended in the solution was collected by filtration and dried at about 55° C. Then, the differential scanning calorimetry was carried out, whereby it was confirmed that the entire amount was maintained to be β-crystals.

EXAMPLE 12

In the same manner as in Example 11, heating was carried out at 65° C. for 16 hours. Then, a part of quizalofop-p-ethyl suspended in the solution was collected by filtration and dried. Then, the differential scanning calorimetry was carried out, whereby it was confirmed that the entire amount had been converted to β-crystals.

Then, the warm water in the jacket was withdrawn, and the above suspension solution was cooled. After cooling, quizalofop-p-ethyl suspended in the solution was collected by filtration at room temperature and dried at about 60° C. Then, the differential scanning calorimetry was carried out, whereby it was confirmed that the entire amount was maintained to be β-crystals.

EXAMPLE 13

In the same manner as in Example 11, heating was carried out at 60° C. for three days. Then, a part of quizalofop-p-ethyl suspended in the solution was collected by filtration and dried. Then, the differential scanning calorimetry was carried out, whereby it was confirmed that the entire amount had been converted to β-crystals.

Then, the warm water in the jacket was withdrawn, and the above suspension solution was cooled. After cooling, quizalofop-p-ethyl suspended in the solution was collected by filtration at room temperature and dried at about 45° C. Then, the differential scanning calorimetry was carried out, whereby it was confirmed that the entire amount was maintained to be β-crystals.

EXAMPLE 14

In the same manner as in Example 11, heating was carried out at 67.5° C. for 10 hours. Then, a part of quizalofop-p-ethyl suspended in the solution was collected by filtration and dried. Then, the differential scanning calorimetry was carried out, whereby it was confirmed that the entire amount had been converted to β-crystals.

Then, the warm water in the jacket was withdrawn, and the above suspension solution was cooled. After cooling, quizalofop-p-ethyl suspended in the solution was collected by filtration at room temperature and dried at about 60° C. Then, the differential scanning calorimetry was carried out, whereby it was confirmed that the entire amount was maintained to be β-crystals.

EXAMPLE 15

Into a 1,000 l jacketed agitation tank, 25 kg of α-crystals of quizalofop-p-ethyl containing 0.2 wt % of β-crystals, and 475 kg of water, were charged to prepare a 5 wt % suspension solution. Warm water was circulated to the jacket, and the suspension solution was heated to 70° C. with stirring. Eight hours later, a part of quizalofop-p-ethyl suspended in the solution was collected by filtration and dried. Then, the differential scanning calorimetry was carried out, whereby it was confirmed that the entire amount had been converted to β-crystals.

Then, the above suspension solution was subjected to filtration by a 65 l centrifugal separator. The product was dried at 60° C. by a 600 l conical drier in vacuum to obtain a dried product of β-crystals of quizalofop-p-ethyl.

What is claimed is:

1. A method for producing β crystals of the compound, ethyl(R)-2[4-(6-chloroquinoxalin-2-yloxy)phenoxy]propionate, comprising heating the α crystals, or the mixture of α and β crystals of said compound, within a range of from 50° C. to lower than the melting point of α crystals, wherein said heating is carried out by heating a suspension of the α crystals, or the mixture of α and β crystals in water.

2. The method according to claim 1 wherein said suspension is from 1 to 60 wt. % based on water.

3. The method according to claim 1 wherein said suspension is from 0.1 to 60 wt. % based on water.

4. The method according to claim 1 wherein said heating is carried out for a period of time from 10 minutes to 48 hours.

5. The method according to claim 1 wherein said heating is within a range of 60° C. to lower than the melting point of the α crystals.

6. The method according to claim 1 wherein said heating is within a range of 65° C. to lower than the melting point of the α crystals.

7. The method according to claim 1 wherein said heating is within a range of 70° C. to lower than the melting point of the α crystals.

* * * * *